United States Patent [19]

Debs et al.

[11] Patent Number: 5,364,615
[45] Date of Patent: Nov. 15, 1994

[54] PROPHYLAXIS OF PNEUMOCYSTIS CARINII WITH AEROSILIZED PENTAMIDINE

[75] Inventors: Robert J. Debs, Mill Valley; Alan B. Montgomery, Redwood City; John E. Conte, Corte Madera; Jeffrey A. Golden, San Francisco, all of Calif.

[73] Assignee: Regents of the University of California, Oakland, Calif.

[21] Appl. No.: 928,534

[22] Filed: Aug. 13, 1992

Related U.S. Application Data

[63] Continuation of Ser. No. 665,332, Mar. 6, 1991, abandoned, which is a continuation of Ser. No. 532,263, Jun. 1, 1990, abandoned, which is a continuation-in-part of Ser. No. 485,042, Feb. 26, 1990, abandoned, which is a continuation of Ser. No. 355,134, May 16, 1989, abandoned, which is a continuation of Ser. No. 180,414, Apr. 12, 1988, abandoned, which is a continuation-in-part of Ser. No. 137,208, Dec. 23, 1987, abandoned.

[51] Int. Cl.$^5$ .................... A61L 9/04; A61K 31/155
[52] U.S. Cl. ........................ 424/45; 239/338; 514/631; 514/637
[58] Field of Search ............... 424/45, 88; 239/338; 514/809, 357, 394, 631, 637

[56] References Cited

U.S. PATENT DOCUMENTS

| | | | |
|---|---|---|---|
| 3,236,458 | 2/1966 | Ramis | 239/318 |
| 3,992,516 | 11/1976 | Lim | 424/8 |
| 4,253,468 | 3/1981 | Lehmbeck | 127/726 |
| 4,268,460 | 5/1981 | Boiarski | 261/1 |
| 4,325,967 | 4/1982 | Caton | 424/299 |
| 4,619,942 | 10/1986 | Tidwell | 514/415 |
| 4,649,911 | 3/1987 | Knight et al. | 128/200.21 |
| 4,719,221 | 1/1988 | Morrison | 514/357 |
| 4,757,049 | 7/1988 | Plotnikoff | 514/17 |
| 4,853,416 | 8/1989 | Anaebonam | 514/636 |
| 4,933,347 | 6/1990 | Tidwell | 514/256 |
| 5,049,388 | 9/1991 | Knight et al. | 424/450 |
| 5,262,157 | 11/1993 | Bernard et al. | 424/45 |

FOREIGN PATENT DOCUMENTS 88310395.4 6/1987 European Pat. Off. .
3533494 3/1987 Germany .

OTHER PUBLICATIONS

Medical World News Jun. 1987.
Girard et al., Antimicrobial agents 31, p. 978, 1987.
Waldman et al., Ann. Rev. of Resp. Diseases 108, 1973, 1004.
Montgomery et al., Lancet 29th Aug. 1987, p. 480.
George J. Jakab and Gareth M. Green, Effects of Pneumonia on Intrapulmonary Distribution of Inhaled Particles, *American Review of Respiratory Disease*, vol. 107: (1975).
Dolovich et al., Aerosol Penetration into the Lung, *Chest* Supplement, 80:834–836 (1981).
Debs et al., Selective Lung Delivery of Pentamidine by Liposomes, *Abstract of the 1985 ICAAC*, Abstract No. 550, p. 192 (1985).
Bernard et al., Aerosol Administration Improves Delivery of Pentamidine to the Lungs, *Abstract of the 1985 ICAAC*, Abstract No. 552, p. 193 (1985).
Debs et al., Successful Treatment of Pneumocystis Carinii Pneumonia in Rats with Aerolsized Pentamidine, *International Conference on AIDS*, Poster 294, Paris, France, (23–25 Jun. 1986).

(List continued on next page.)

Primary Examiner—G. S. Kishore
Attorney, Agent, or Firm—Hana Dolezalova

[57] ABSTRACT

A method of preventing clinically manifest *Pneumocystis carinii* pneumonia in immunocompromised humans is provided wherein an aerosol of pentamidine is administered to the patient in a manner which delivers the aerosol to the patient's alveoli. Also provided is a method of treating *Pneumocystis carinii* pneumonia in HIV seropositive individuals comprising administering a therapeutically effective amount of pentamidine aerosol to the HIV positive individual through inhalation. In addition, a method is provided of administering pentamidine to a human comprising aerosolizing a pentamidine solution in a nebulizer system having a one-way valve disposed between the nebulizer and the mouthpiece of the nebulizer system.

7 Claims, 1 Drawing Sheet

OTHER PUBLICATIONS

Brennessel D. J., and Goldstein J. A., Eflornithine Hydrochloride (DFMO) in the Therapy (rx) of Penumocystis Carinii Pneumonia (PCP) in AIDS, *International Conference on AIDS*, Poster 295, Paris, France, (23–25 Jun. 1986).

Kaplan et al., Trimethoprim-Sulfamethoxazole (TMP-SMZ) Prophylaxis of Pneumocystis Carinii Pneumonia (PCP) in AIDS, *International Conference on AIDS*, Poster 299, Paris, France, (23–25 Jun. 1986).

Bernard et al., *International Conference on AIDS*, Poster 300, Paris, France, (23–25 Jun. 1986).

Wharton et al., Trimethoprim-Sulfamethoxazole or Pentamidine for Pneumocystis Carinii Pneumonia in the Acquired Immunodeficiency Syndrome, *Annals of Internal Medicine*, 105:37–44 (1986).

Donnelly, et al., Distribution of Pentamidine in Humans, *Abstracts of the 1986 ICAAC*, Abstract 696, p. 225 (1986).

Debs, R., Targeting of Drugs and Immunodulators for the Treatment of AIDS-Related Opportunistic Infections, *The University-wide Task Force on AIDS Annual Meeting*, Poster Session, San Diego, CA, (Mar. 19–20, 1987).

Conte et al., Inhaled or Reduced-Dose Intravenous Pentamidine for Pneumocystis Carinii Pneumonia, *Annals of Internal Medicine*, vol. 107; 495 (Oct. 1987).

Montgomery et al., Concentration of Pentamidine in Bronchoalveolar Lavage Fluid After Aerosol and Intravenous Administration, *4H AIDS/Poster Symposium (MTPI) Monday 2:00–5:00 pm, Carondelet Ballroom (MH)*, A167.

Debs et al., Selective Enhancement of Pentamidine Uptake in the Lung by Aerosolization and Delivery in Liposomes, *Am. Rev. Respir. Dis.* 135:731 (Mar. 1987).

Montgomery et al., Aerosolized Pentamidine as Sole Therapy for Pneumocystis Carinii Pneumonia in Patients with Acquired Immunodeficiency Syndrome, *The Lancet*, pp. 480–483 (Aug. 29, 1987).

Debs et al., Successful Treatment with Aerosolized Pentamidine of Pneumocystis Carinii Pneumonia in Rats, *Antimicrobial Agents and Chemotherapy*, 31:37–41 (Jan. 1987).

James, J. S., A Breakthrough in Treating Pneumocystis?, *San Francisco Sentinel*, 15(3):1 (Jan. 16, 1987).

James, J. S., Aerosol Pentamidine: New PCP Prophylaxis and Treatment, *Aids Treatment News*, Issue No. 23, (Jan. 16, 1987).

Jesuthasan et al., Aerosolised Pentamidine, *The Lancet*, p. 971 (Oct. 24, 1987).

Paton, Aerosolised Pentamidine, *The Lancet*, p. 1146 (Nov. 14, 1987).

Heley, Aerosolized Pentamidine Treatment at Home, *The Lancet*, p. 1092 (Nov. 7, 1987).

Brain et al., Deposition of Aerosol in the Respiratory Tract, *American Review of Respiratory Disease*, vol. 120:1325–1373 (1979).

*Ann. Int. Med.*, 103:782 (1985).

Conte, J. et al., Use of Specific and Sensitive Assay to Determine Pentamidine Pharmacokinetics in Patients awith AIDS, 1986 *International AIDS Conference*, Poster 296 Jun. 1986.

FIG. 1

PROPHYLAXIS OF PNEUMOCYSTIS CARINII WITH AEROSILIZED PENTAMIDINE

This is a continuation of copending application of Ser. No. 07/665,332 filed on Mar. 6, 1991, abandoned, which is a continuation of U.S. patent application Ser. No. 07/532,263, filed Jun. 1, 1990, abandoned which is a continuation-in-part of U.S. patent application Ser. No. 485,042, filed Feb. 26, 1990, now abandoned which is a continuation of U.S. patent application Ser. No. 355,134, filed May 16, 1989, now abandoned, which is a continuation of U.S. patent application Ser. No. 180,414, filed Apr. 12, 1988, now abandoned, which is a continuation-in-part of U.S. patent application Ser. No. 137,208, filed Dec. 23, 1987, now abandoned, all of which are incorporated herein by reference.

TECHNICAL FIELD

The present invention relates to the treatment of *Pneumocystis carinii* infection, particularly *P. carinii* pneumonia (PCP), via the aerosol administration of the drug pentamidine to the respiratory system of a patient suffering from such infection.

BACKGROUND

Severe *Pneumocystis carinii* infections of immunocompromised individuals, such as premature infants, children with hypogammaglobulinemia or deficiencies of cell-mediated immunity, patients receiving immunosuppressive therapy, and patients suffering acquired immunodeficiency syndrome (AIDS), leads to the development of *Pneumocystis carinii* pneumonia (PCP). By far the most common occurrence of PCP is in AIDS patients. More than 36,000 cases of AIDS have been reported since 1979, and 62% of these patients developed PCP ("Acquired Immunodeficiency Syndrome (AIDS) Weekly Surveillance Report", CDC (Dec. 29, 1986)). With current standard treatments, mortality for the first episode of PCP in AIDS patients is approximately 20–30%. To date, over 42,000 cases of PCP have been reported in AIDS patients (including multiple episodes), with 100,000 cases predicted to occur in the United States by 1991.

The two conventional therapies for treating PCP consist of either trimethoprim-sulfamethoxazole (TMP-SMX) administered orally or parenterally, or pentamidine isethionate administered parenterally: Hughes et al, *J Pediatr* (1978) 92:285–291; Sattler et al, *Am J Med* (1981) 70:1215–1221; Navin et al, *N Engl J Med* (1984) 311:1701–1702. Unfortunately, approximately 50% of patients receiving either drug treatment develop severe toxicity, requiring discontinuation of the therapy: e.g., K. A. Western et al, *Ann Int Med* (1970) 73:695; M. Wharton et al, *Ann Int Med* (1985) 105:37–44; F. M. Gordin et al, *Ann Intern Med* (1984) 100:495–499. Many immediate and long term side effects have been associated with the parenteral administration of pentamidine. Pain, swelling and sterile abscesses are observed at the site of intramuscular injections, and thrombophlebitis and generalized or localized urticarial eruptions are associated with intravenous administration. Severe hypotension may also develop following a single intramuscular dose, or after rapid intravenous infusion: Navin et al, supra. Hypoglycemia has also been reported in patients: Walzer et al, supra; Pearson et al, *Ann Inter N Med* (1985) 103:782–786. In some patients with hypoglycemia, diabetes mellitus also develops: Osei et al, *Am J Med* (1984) 77:41–46. Impaired renal function occurs in about 25% of patients receiving pentamidine. Other common adverse reactions include elevation of liver enzymes, hematologic disturbances with neutropenia and thrombocytopenia, fever, hypocalcemia, and hallucinations. Less common adverse effects include cardiac arrhythmias and pancreatitis. See, e.g., Pearson et al, supra.

When a patient develops an adverse reaction requiring discontinuance of one of the above standard therapies, the usual recourse is to place the patient on the alternative standard therapy. A substantial number of patients, however, develop an adverse reaction to both TMP-SMX therapy and parenteral pentamidine. Thus, the art has actively pursued alternative therapies that obviate the serious side effects associated with the above standard therapies. For example, dapsone (diaminodiphenylsulfone) has been tried both alone and in combination with TMP, to treat PCP. Dapsone has been reported to be effective in a rat PCP model: Hughes et al, *Antimicrobial Aqents Chemother* (1984) 26:436. Dapsone alone, however, has a failure rate for PCP of about 39%, while approximately 31% of the patients given trimethoprim-dapsone (TMP-DPS) experienced severe toxicity: G. S. Leoung et al, *Ann Int Med* (1986) 105:45–48; Mills et al, Int'l. Conf. on AIDS, poster 297 (Paris, France, 23–25 June 1986); Medina et al, Proceedings of the III Int'l. Conf. on AIDS, p. 208 (Washington, D.C. 1987).

Another alternative therapy is treatment with α-difluoromethylornithine (DFMO). Although DFMO was hot efficacious in a rat model of PCP, recent clinical studies report some clinical response for this drug: J. A. Golden et al, *West J Med* (1984) 141:613; McLees et al, *Am Rev Respir Dis* (1987) 135:A167. Yet another potential therapy for PCP has been suggested using the drug trimetrexate. Adverse reactions have been reported, however, and the relapse rates within one month appear to be high: Allegra et al, *N Engl J Med* (1987) 317:978–985.

The aerosolization of pentamidine has been studied in rodent models: R. H. Waldman et al, *Am Rev Respir Dis* (1973) 108:1004–1006; R. J. Debs et al, Abstracts of the 1985 ICAAC, p. 192 (Abstract No. 550); E. H. Bernard et al, Id. p. 193 (Abstract No. 552); R. J. Debs et al, Int'l. Conf. on AIDS, poster 294 (Paris, France 23–25 June 1986); E. H. Bernard et al, Id., poster 300.

AIDS patients suffering PCP are known to have higher rates of adverse reaction to certain therapies than other immunocompromised patients suffering PCP: Hughes et al, supra; Gordin et al, supra. Thus, the art is in need of a more effective therapy for PCP, particularly in AIDS patients, and none of the known or potential routes of therapy have demonstrated the ability to be both efficacious and free of adverse side effects.

SUMMARY OF THE INVENTION

It has surprisingly been discovered that an aerosol of pentamidine having particle sizes within the range of about 0.25 to about 2.5 microns ($\mu$m) delivered by inhalation to the respiratory system of a patient infected with *Pneumocystis carinii* effectively inhibits the *P. carinii* infection without causing systemic side effects. Furthermore, it has been discovered that the aerosol treatment with pentamidine is even effective for clinically manifest infections, such as PCP in AIDS patients. Thus, it has been demonstrated that therapeutically effective amounts of aerosolized pentamidine can be delivered by inhalation to the human lung, even diseased lungs, while systemic levels of pentamidine remain sufficiently low to prevent the adverse side effects associated with parenteral pentamidine therapy. Indeed, it appears that aerosol pentamidine therapy does not suffer any of the drawbacks associated with standard PCP therapies, yet is highly efficacious in the treatment of at least mild to moderate PCP. We have found that treatment using aerosolized pentamidine is effective even in patients forced to discontinue treatment with parenteral pentamidine due to toxicity. In view of this unexpected combination of efficacy and safety, aerosolized pentamidine is becoming the therapy of choice for Pneumocystis carinii infection in AIDS patients. This treatment has been approved by the U.S. Food and Drug Administration.

In its broadest aspects, the present invention is directed to a method of inhibiting *P. carinii* pulmonary infections in a human patient comprising delivering, by inhalation to the respiratory system of a patient suffering from *Pneumocystis carinii* infection, an aerosol of pentamidine having particle sizes of which some fall within the range of about 0.25 μm to about 5.0 μm, preferably within the range of about 0.5 to about 2.5 μm, in an amount sufficient to effect treatment of *Pneumocystis carinii* infection. The pentamidine aerosol is preferably generated and delivered to the patient by a suitable medical nebulizer. Suitable medical nebulizers include, but are not limited to, the Respirgard ® II and the UltraVent ®. For patients with sub-clinical *Pneumocystis carinii* infections, the amount of pentamidine aerosol sufficient to effect treatment is delivered to the patient's respiratory system when about 20 mg to about 600 mg, preferably about 30 to about 300 mg, of pentamidine is aerosolized and then administered to the patient's respiratory system by inhalation. For treatment of subclinical infections, the drug can be delivered intermittently, preferably by administering pentamidine aerosol once every 2-4 weeks. For patients with clinically manifest *Pneumocystis carinii* infection (e.g., with *Pneumocystis carinii* pneumonia), an amount of pentamidine aerosol sufficient to effect treatment results when about 20 mg to about 600 mg pentamidine is aerosolized and administered. For clinically manifest infections, the pentamidine aerosol is preferably delivered repeatedly to the patient's respiratory system by having the patient inhale the pentamidine aerosol daily for about 4 to 21 days.

In various preferred embodiments of the present invention, the particle size of the aerosol administered to the patient is selected to minimize deposition of pentamidine in the airways, and therefore increase the amount drug delivered to alveoli. The method of the present invention is preferably employed with HIV-infected patients, particularly those suffering from AIDS or AIDS-related complex (ARC), to prevent latent or subclinical *P. carinii* infections from developing into clinically manifest forms, as well as with HIV-positive patients to treat clinically manifest *P. carinii* infections such as *Pneumocystis carinii* pneumonia (PCP). Other preferred embodiments will be apparent from the detailed description and the examples.

DETAILED DESCRIPTION

*Pneumocystis carinii* are organisms that invade the lungs of humans early in childhood, and remain there throughout life. In a healthy person these organisms are maintained at low or "subclinical" levels by the immune system. However, if the individual's immune system is depressed, the ability to keep *Pneumocystis carinii* at subclinical levels is lost. Consequently, the number of *Pneumocystis carinii* present in the lung increases, which in turn leads to pathologies or disease states that include inflammation of lung tissue. This inflammation, among other things, prevents the alveolar portions of the lungs from performing their normal function of gas exchange. As the inflammation increases, patients begin to develop symptoms such as fever and cough, and find it increasingly difficult to breath. When the inflammation and other pathologies become clinically manifest and reach certain clinically defined levels, the patient is diagnosed as having *Pneumocystis carinii* pneumonia, or PCP for short.

"Prophylactic" treatment for *P. carinii* infection as used herein refers to treatment which prevents subclinical infection from developing into a clinically recognizable infection such as *Pneumocystis carinii* pneumonia (PCP). Such prophylactic treatment is known as post-exposure prophylaxis. Post-exposure prophylaxis refers to administration of a drug to a patient (1) after the patient has come in contact with the infecting organism, (2) for the purpose of preventing the spread of the infection, i.e., the organism. As used herein, "treatment" of *P. carinii* pulmomary infection includes both treatment of clinically manifest *Pneumocystis carinii* infection (such as PCP) and prevention of clinically manifest *Pneumocystis carinii* infection (i.e., maintenance of *Pneumocystis carinii* infection at subclinical levels).

The method of the present invention is particularly useful for treating immunocompromised human patients. Such patients include individuals suffering from AIDS or ARC, as well as premature infants, patients treated with immunosuppressive drugs, and patients afflicted by other immunocompromising diseases or defects. The present invention is particularly useful in the treatment of AIDS and ARC patients, such patients being defined by generally accepted clinical diagnostic criteria. The method of the present: invention is also believed to be useful for HIV-positive individuals (patients seropositive for HIV particles, fragments or anti-HIV antibodies) who have not yet developed AIDS or ARC, but who are considered to be at risk for PCP. Further, in some instances it may be desirable to treat subjects at or before the time that the subject is immunosuppressed, for example, during or prior to scheduled chemotherapy. A patient "at risk" for *P. carinii* pulmonary infection or PCP is any patient for whom a substantial possibility exists that clinically recognizable *Pneumocystis carinii* infection or PCP will develop. For the most part, "at risk" patients are those patients who are immunosuppressed or immunocompromised.

As used herein, "pentamidine" refers to the drug p,p'-(pentamethylenedioxy)dibenzamidine and its pharmaceutically acceptable salts. See, e.g., U.S. Pat. No. 2,410,769. Various salts can be prepared by those of skill in the art by known techniques. The salt form of the drug is particularly preferred to improve solubility in the solution to be aerosolized. The most popular form of the drug is pentamidine isethionate, which is the bis(β-hydroxyethane sulfonate) salt. Since sulfur oxides such as the isethionate and mesylate salts may induce bronchoconstriction when inhaled (particularly by persons with hyperreactive airways), it may be desirable to avoid the use of sulfur oxide salts for certain patients. For example, pentamidine glutamate, pentamidine lactate, and pentamidine hydrochloride may be employed as alternatives to sulfur oxides. Pentamidine salts are available from various commercial sources, such as Lyphomed, Melrose Park, Ill. and Aldrich Chemical Co., Milwaukee, Wis.

Pentamidine, usually as a salt, is made into a solution or suspension for aerosolization. The exact concentration and volume of the solution are not critical, acceptable formulations being readily determined by those of ordinary skill in the art. The exact concentration and volume of the solution will generally be dictated by the particular nebulizer selected to deliver the drug, and the intended dose. It is preferred to minimize the total volume, however, to prevent unduly long inhalation times for the patient.

The pentamidine solution is aerosolized by any appropriate method. Usually, the pentamidine aerosol will be generated by a medical nebulizer system which delivers the aerosol through a mouthpiece, facemask, etc. from which the patient can draw the aerosol into the lungs. Various nebulizers are known in the art and can be used in the method of the present invention. See, e.g., Boiarski et al, U.S. Pat. No. 4,268,460; Lehmbeck et al, U.S. Pat. No. 4,253,468; U.S. Pat. No. 4,046,146; Haystad et al, U.S. Pat. No. 3,826,255; Knight et al, U.S. Pat. No. 4,649,911; Bordoni et al, U.S. Pat. No. 4,510,929.

In selecting a nebulizer system, it is preferred to select a system which will effectively deliver substantial quantities of the drug to the pulmonary alveoli. Improper technique can result in deposition only within the airways (i.e., trachea, pharynx, bronchi, etc.), with either little or no drug reaching the alveoli and the situs of *Pneumocystis carinii* infection. A convenient way to insure effective delivery of the drug to the alveoli is to select a nebulizer which produces sufficiently small particles (e.g., about 0.25 to about 5.0 $\mu$m, preferably about 0.5 to about 2.5 $\mu$m), since the larger particles are generally deposited in the airway or nasopharynx. Usually, this can be accomplished by aerosolizing the pentamidine in a manner that provides a mean maximum particle diameter (measured as described in the Examples) of about 4–5 $\mu$m or less. It is preferred to have a maximum mean particle diameter of about 3 $\mu$m or less, and most preferably about 2.5 $\mu$m or less. The preferred range of mean particle diameter is generally about 0.50 to about 2.5 $\mu$m.

As an alternative to selecting small mean particle diameters to achieve substantial alveoli deposition, it may be possible to administer a very high dosage of pentamidine with a larger mean particle diameter. A proviso to such an approach is that the pentamidine salt selected is not too irritating at the required dosage and that there are a sufficient number of particles in the total population having a diameter in the 0.5 to about 5 $\mu$m range to allow for deposition in the lungs.

Figure 1:
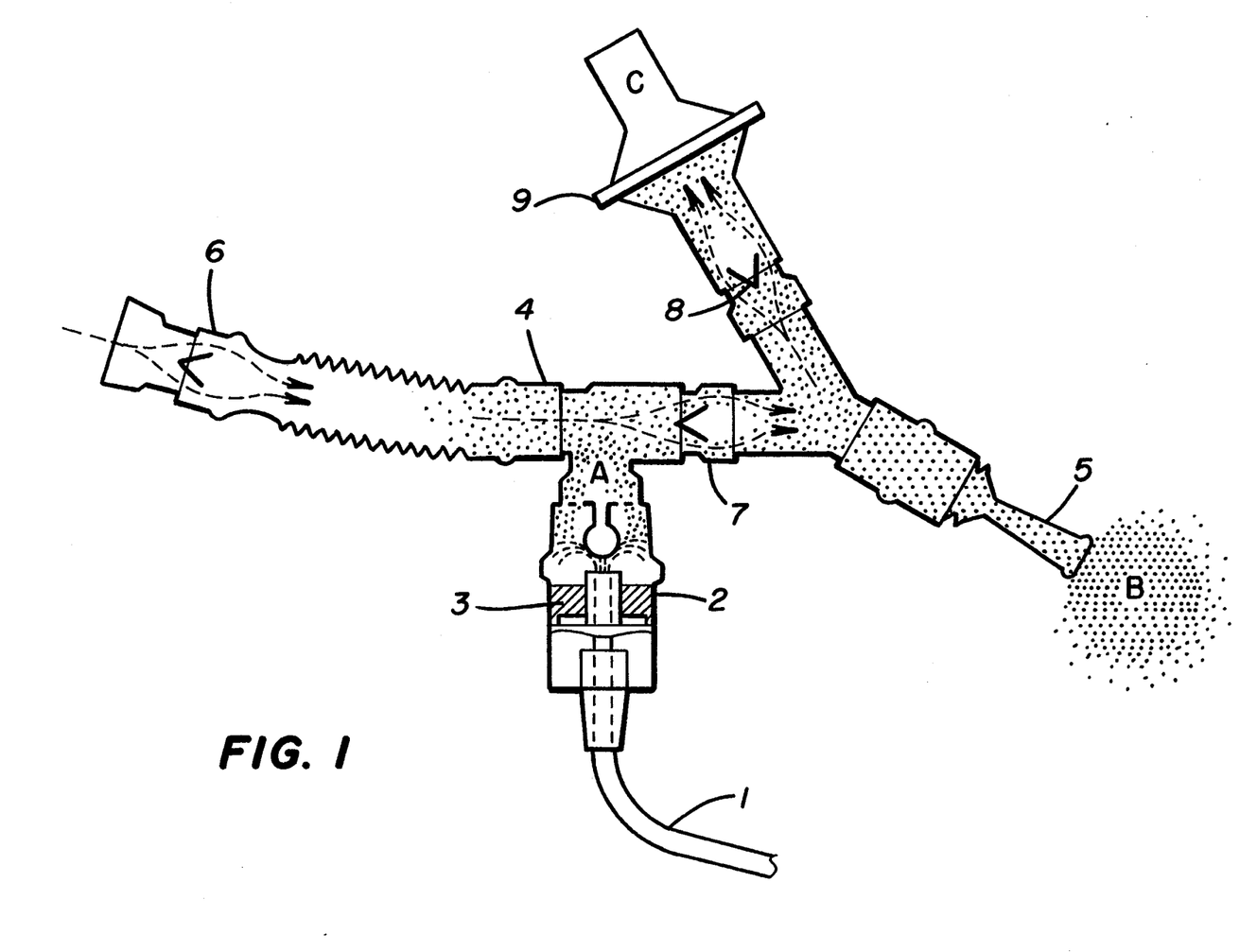
FIG. 1 is a diagram showing a nebulizer system useful for producing and administering pentamidine aerosol.

An example of a medical nebulizer that can be used in the practice of the present invention is shown in FIG. 1. This nebulizer, available commercially from Marquest Medical Products, Inc., Inglewood, Colo. (Respirgard II ® Nebulizer System, Product No. 124030), is an inexpensive disposable nebulizer system that can aerosolize pentamidine solutions and produce particles having a mean diameter in the range of about 1–2 $\mu$m. In the preferred mode of operation for this nebulizer, referring to FIG. 1, oxygen flows through tube 1, usually at a rate of about 5 to about 7 L/min, preferably about 6 L/min, into nebulizer 2, where pentamidine solution 3 is aerosolized, generating particles in conduit 4. When a patient draws on mouthpiece 5, air is drawn through one-way valve 6, and the airstream entrains the pentamidine particles in conduit 4. As the airstream containing the pentamidine aerosol passes around the baffle of one-way valve 7, the population of large particles (i.e., diameter greater than about 2–4 $\mu$m) is substantially reduced, so that the particles leaving the mouthpiece 5 have a mean diameter in the range of about 1 to about 2 $\mu$m. When the patient exhales through mouthpiece 5, the vented gas containing pentamidine particles travels through one-way valve 8 towards particle filter 9, which removes any residual pentamidine particles from the stream. Thus, the exhaled gas leaving the nebulizer system through particle filter 9 is free of pentamidine, minimizing the exposure of attending personnel. Other suitable nebulizers for use with the method of the invention include without limitation the UltraVent ® nebulizer available from Mallinckrodt, Inc. (Maryland Heights, Mo.); the Wright nebulizer (B. M. Wright, Lancet (1958) 3:24–25); and the DeVilbiss nebulizer (T. T. Mercer et al, *Am Ind Hyg Assoc J* (1968) 29:66–78; T. T. Mercer, Chest (1981) 80:6(Sup) 813–17).

As indicated above, *Pneumocystis carinii* infect the alveoli. Therefore, a key aspect of the present invention is delivering effective amounts of the drug pentamidine to the patient's alveoli. While there is no direct method of measuring the amount of pentamidine delivered to the alveoli, bronchoalveolar lavage (BAL) can be used to indirectly measure alveolar concentrations of the drug, usually 18–24 hrs after inhalation to allow clearance of pentamidine deposited in the bronchi. It should also be understood that the amount of pentamidine deposited in the alveoli may be substantially less than the total amount aerosolized since a large portion is exhaled by the patient or is trapped on the interior surfaces of the nebulizer apparatus. For example, approximately one third of the pentamidine dose that is placed into the nebulizer remains in the nebulizer after inhalation is completed. This is true regardless of the dose size, duration of inhalation, and type of nebulizer used, Respirgard or Ultravent. Moreover, resuspension of the residue and readministration does not significantly increase the dose delivered to the patient: about one third remains in the nebulizer. Furthermore, even with minimization of airway deposition, there is a portion which is still deposited in the patient's airways.

As used herein, with reference to drug dosages and especially "effective amounts of drug to effect treatment", "pentamidine aerosol" refers to the amount of drug that is placed in the nebulizer and subjected to aerosolization. The "amount nebulized" or "amount aerosolized" of the drug means the amount that actually leaves the apparatus as an aerosol, i.e., the amount placed into the apparatus less the amount retained in the reservoir and on the inner surfaces of the apparatus at the conclusion of a treatment session. "Treatment of pentamidine delivered to the alveoli" refers to the amount of drug that is estimated to actually reach the alveoli. As used herein, an "effective amount" of aerosolized pentamidine is that amount which is sufficient to effect treatment, that is, to cause alleviation or reduction of symptoms, to inhibit the worsening of symptoms, to prevent the onset of symptoms, and the like.

The total amount of the drug delivered to the alveoli will depend upon many factors, including the total amount aerosolized, the type of nebulizer, the particle size, patient breathing patterns, severity of disease, concentration of pentamidine in the aerosolized solution, and length of inhalation therapy. Despite these interacting factors, one of ordinary skill in the art will be able to readily design effective protocols, particularly if the particle size of the aerosol is minimized. Depending on the above factors, it is believed that the efficiency of delivery by inhalation is about 7–10%. Based on estimates of nebulizer efficiency, it is believed that as little as about 1 mg/treatment of pentamidine actually delivered to the alveoli will inhibit *P. carinii* infections. Preferably, at least about 5 mg/treatment is delivered to the alveoli, more preferably at least about 10 mg/treatment. An effective dose delivered to the alveoli will probably lie in the range of about 1 mg/treatment to about 100 mg/treatment, and preferably about 20 mg/treatment to about 75 mg/treatment, although more or less may be found to be effective depending on the patient and desired result. It is generally desirable to administer higher doses when treating more severe infections. For severe infection, it is preferred to adminster about one treatment per day.

Single discrete doses of aerosolized pentamidine may be administered, usually in the lower range of the dosages described above, for treatment of subclinical *P. carinii* infections to prevent PCP. Of course, higher dosages capable of treating clinically manifest infections are also effective against subclinical infections. The frequency of treatments depends upon a number of factors, such as the amount of pentamidine administered in the single dose, the health of the individual, and the patient's history of PCP infections. In general, it is preferred that there be at least about one week between treatments, generally about two to about four weeks, and possibly from about two to about three months. This extended interval between treatments is possible due to the long halflife of pentamidine in the lungs (e.g., about 3–6 weeks).

When treating clinically manifest *P. carinii* infections such as PCP, it will usually be necessary to administer at least one aerosol dose per day to the patient for a period of about 4 to about 21 consecutive days or longer. Despite the long halflife of pentamidine in the lungs, the treatment is usually carried out on consecutive days because new areas of the lungs open up to penetration and deposition of the drug with increasing resolution of the pneumonia. It is preferred to deliver at least about 20 mg/day to the alveoli, more preferably at least about 30 mg/day, and most preferably at least about 40 mg/day. The therapy will usually be administered daily over a full 21 day period, unless the treatment for PCP results in a successful response before the end of the treatment, as judged by conventional clinical criteria; e.g., clearing of radiographic infiltrate, improved arterial $PO_2$ (e.g., >70 mmHg), reduction in dyspnea, respiratory rate and/or fever.

When employing the nebulizer system depicted in FIG. 1, it is desirable to nebulize at least about 15 mg of pentamidine, more preferably at least about 50 mg of pentamidine, and most preferably at least about 100 mg. A preferred amount to nebulize will be in the range of about 30 mg to about 600 mg. Higher dosages can be employed, particularly with the non-sulfur oxide salts (to minimize irritation), due to the low toxicity of aerosolized pentamidine. To achieve aerosolization of the above amounts with the above device, and employing a 6 mL volume of pentamidine solution, it will generally be necessary to place from about 30 mg to about 600 mg of pentamidine into the solution. With other nebulizers the amounts may vary; however, provided appropriate attention is paid to particle size, the selection of appropriate amounts to obtain efficacious doses is within the skill of the art in view of this disclosure. For example, dosage levels with appropriate safety factors can be established by comparing results from a bronchoalveolar lavage to the results obtained from a lavage after treatment with the above nebulizer system or effective intravenous therapy (see, e.g., Example 1).

By way of illustration with the nebulizer system shown in FIG. 1, an effective protocol to treat PCP is to dissolve about 600 mg of pentamidine isethionate (Pentam® 300, Product No. 113-10, LyphoMed, Melrose Park, Ill.) in about 6 mL of sterile water or other pharmaceutically acceptable carrier, place the solution into the nebulizer, adjust the oxygen flow to approximately 6 L/min, have the patient breathe normally from the nebulizer through the mouth until approximately 3–4 mL of the solution has been nebulized. The treatment time varies, usually from about 15 to about 30 min, depending on patient tolerance, and it is estimated that the absorbed dose from such a protocol is about 45–60 mg. Repeating this dosage sequentially for a period of at least about 4 days to about 21 days has been found to be an effective treatment for AIDS patients suffering PCP. As a prophylactic for PCP, lower dosages can adequately inhibit *P. carinii* infection. For example, about 50 mg to about 300 mg is dissolved into 6 mL and aerosolized, and one treatment is administered every 2–8 weeks. Preferably, about 50 to about 300 mg is aerosolized and administered once every 2–5 weeks, most preferably once every 4 weeks.

The only frequent adverse effect observed clinically from the administration of aerosolized pentamidine is transient airway irritation. Patients with hyperreactive airways, such as patients with asthma or heavy cigarette smokers, may experience some difficulty with aerosolized pentamidine isethionate. This irritation, manifested as coughing during treatment and possibly chest tightness, can be relieved for some patients by the inhalation of bronchodilatory agents. The side effect may also be avoided by employing other salts of pentamidine, such as the glutamate, lactate or hydrochloride, which do not contain irritating sulfur oxides.

The following examples are provided for illustrative purposes only and do not limit the scope of the present invention.

EXAMPLE 1

(Treatment of *Pneumocystis carinii* Pneumonia)

A prospective, nonrandomized study was conducted using human patients presenting mild to moderate PCP, defined as: histologic confirmation of the diagnosis, arterial blood oxygen tension (PaO2) greater than 55 mmHg on room air, and likely to maintain present clinical status for at least four days, even without specific therapy. The study was approved by the Human Research Committee at the University of California at San Francisco, and written informed consent obtained from each patient. Patients were excluded if they had received pentamidine therapy for PCP within the previous three months. Patients whose condition deteriorated clinically within four days after enrollment were placed on conventional therapy and listed as "not evaluated."

Diagnosis of PCP was confirmed by either bronchoalveolar lavage (C. Broaddus et al, *Ann Intern Med* (1985) 102:747-52; D. C. Zavala et al, *Flexible Fiberoptic Bronchoscopy*, (1978, Pepco Litho Place, Cedar Rapids, Iowa)), or by sputum induction (T. D. Bigby et al, *Am Rev Respir Dis* (1986) 133:515-18). The fluid was examined with Gram's stain, uranium stain, potassium hydroxide (E. H. Lennette et al, *Manual of Clinical Microbiology*, 4th ed., (1985, Amer. Soc. for Microbiology, Washington D.C.), and for *P. carinii*, using the methods described by J. A. Golden et al, *Chest* (1986) 90:18-22; and H. K. Kim et al, *Am J Clin Pathol* (1973) 6:462-66. Fluid was inoculated onto media for bacterial (including Legionella), fungal and viral isolation.

Pulmonary function testing was performed within one week of therapy in 18 of 19 patients who were tested, using methods described in the literature (M. M. Mitchell et al, *Am Rev Respir Dis* (1968) 97:571-80; R. O. Crapo et al, *Am Rev Respir Dis* (1981) 123:659-64; C. H. Ogilvie et al, *J Clin Invest* (1957) 36:1-17; A. F. Gelb et al, *Am Rev Respir Dis* (1973) 107:50-63; and H. I. Goldman et al, *Am Rev Tuberc* (1959) 79:457-63).

The treatment regimes were as follows:
(A) Inhaled pentamidine (N=13):4 mg/Kg administered using a Mallinckrodt UltraVent ® nebulizer over 30-60 minutes (two consecutive 4 mL aliquots);
(B) Intravenous pentamidine (N=9):3 mg/Kg administered as a 2-hour infusion, as long as clinically indicated.

Therapeutic failure was defined as clinical deterioration after four days of treatment, or lack of improvement after one week of treatment.

For six inhalation patients (1, 4, 6, 7, 15, and 16) and five i.v. patients (2, 3, 5, 8, and 22), plasma samples were obtained at the completion of therapy and at 0.17, 0.5, 1, 1.5, 2, 2.5, 3, 4, 5, 6, 8, 10, 12, and 18 hours following initiation of therapy. For patients 9-14 and 17-21, trough and peak plasma samples were collected for the first three days, then weekly during therapy. Trough and peak samples were obtained on days 2, 3, 4, 5, 7, 11, and 13 for patient 2, days 2, 3, 4, 5, 7, and 12 for patient 3, days 2, 3, 4, 5, 13 and 18 for patient 5, and days 2, 3, 4, 5, and 11 for patient 8.

There is no accepted method for precisely determining the volume of alveolar lining fluid. Therefore, pentamidine concentrations are expressed in ng/mL lavage fluid. Fifteen mL aliquots from serially filled suction traps (each containing approximately 35 mL of lavage fluid) were assayed for pentamidine concentration. Pentamidine was determined in plasma, urine, and bronchoalveolar fluid by HPLC, using the technique disclosed by J. E. Conte Jr. et al, *J Infect Dis* (1986) 154:923-29; and R. J. Debs et al, *Am Rev Respir Dis* (1987) 135:731-37. A leukocyte count, hematocrit, platelet count, and tests of alanine aminotransferase (ALT), and glucose were performed weekly, and a creatinine and urinalysis twice weekly. Other clinical and laboratory evaluations were performed as clinically indicated. Three bronchoscopies were permitted by the protocol. The criteria used for major toxicity are described in G. S. Leoung et al, (1986) supra.

The patient characteristics and outcomes are summarized in Table 1. The initial vital capacity, total lung capacity and diffusing capacity for carbon monoxide (all % predicted, mean±SD) for the inhalation (N=10) and intravenous administration (N=8) groups were Inhalation: 78.5±15.1 initial vital capacity; 79.7±15.5 total lung capacity; 64.3±14 diffusing capacity for CO; and Intravenous: 71.5±26.1 initial vital capacity; 77.5±18.0 total lung capacity; 54.4±9.8 diffusing capacity for CO.

TABLE 1

Patient Characteristics and Outcomes

| Patient | Duration of acute symptoms (weeks) | serum creatinine μmol/L (mg/dL) | $PaO_2a$ mmHg | $PaCO_2$ mmHg | Duration of treatment (weeks) | Pentamidine daily (mg) | Pentamidine total (mg) | Time to discharge (days) | Outcome of therapy |
|---|---|---|---|---|---|---|---|---|---|
| Inhalation | | | | | | | | | |
| 1 | 3 | 80(0.9) | 81 | 34 | 5 | 260 | 1300 | 27 | failedd |
| 4b | 2 | 71(0.8) | 67 | ND | 15 | 250 | 3750 | 17 | success |
| 6 | 2 | 88(1.0) | 74 | 42 | 15 | 240 | 3600 | 16 | success |
| 7 | 1 | 80(0.9) | 82 | 39 | 14 | 240 | 3360 | 15 | success |
| 9b | 1 | 53(0.6) | 73 | 22 | 3 | 216 | 648 | 9c | NEd |
| 10 | 1 | 71(0.8) | 75 | 33 | 13 | 210 | 2730 | 14 | success |
| 11 | 3 | 80(0.9) | 62 | 36 | 1 | 280 | 280 | 13 | NEd |
| 12 | 1 | 88(1.0) | 60 | 36 | 14 | 270 | 3780 | 16 | success |
| 13 | 1 | 88(1.0) | 57 | 36 | 3 | 240 | 720 | 13 | NEd |
| 14 | 2 | 71(0.8) | 64 | 36 | 14 | 250 | 3500 | 15 | success |
| 15b | 3 | 80(0.9) | 95 | 34 | 14 | 240 | 3500 | 15 | success |
| 16 | 9 | 71(0.8) | 68 | 36 | 14 | 230 | 3220 | 14 | success |
| 17b | 1 | 80(0.9) | 73 | 34 | 14 | 280 | 3920 | 14 | success |
| All patients in group:f | | | | | 14 ± 0.6 | 247 ± .21 | 3484 ± 356 | 15 ± 1 | |
| Intravenous: | | | | | | | | | |
| 2 | 2 | 71(0.8) | 67 | 38 | 12 | 168 | 2016 | 12 | success |
| 3 | 3 | 115(1.3) | 75 | 30 | 12 | 168 | 2016 | 12 | success |
| 5 | 1 | 80(0.9) | 60 | 37 | 18 | 200 | 3600 | 18 | success |
| 8 | 2 | 62(0.7) | 79 | 37 | 14 | 210 | 2940 | 16e | success |
| 18 | 4 | 62(0.7) | 100 | 33 | 10 | 190 | 1900 | 13 | successd |
| 19 | 1 | 88(1.0) | 73 | 35 | 14 | 264 | 3696 | 14 | success |
| 20 | 2 | 80(0.9) | 63 | 28 | 11 | 165 | 1815 | 16 | successd |
| 21b | 1 | 62(0.7) | 103 | 39 | 14 | 230 | 3220 | 14 | success |
| 22b | 1 | 88(1.0) | 70 | 34 | 9 | 196 | 1764 | 12 | failedd |

TABLE 1-continued

Patient Characteristics and Outcomes

| Patient | Duration of acute symptoms (weeks) | serum creatinine μmol/L (mg/dL) | PaO₂a mmHg | PaCO₂ mmHg | Duration of treatment (weeks) | Pentamidine daily (mg) | Pentamidine total (mg) | Time to discharge (days) | Outcome of therapy |
|---|---|---|---|---|---|---|---|---|---|
| All patients in group:f | | | | | 13 ± 2.5 | 198 ± 35 | 2633 ± 793 | 14 ± 2 | | a Measurements taken with patients breathing room air
b Patient treated previously for *P. carinii* pneumonia
c Patient died on this day
d Patient changed to alternate therapy
e Patient at Moffit/Long Hospital for 3 days, and at a San Francisco hospital 13 days
f Based on 9 successful inhalation patients, and on 8 successful I.V. patients The duration of treatment and time to discharge in days for patients 1–22 were (5, 27), (12, 12), (11, 12), (15, 17), (18, 18), (15, 16), (14, 15), (14, 16), (3, 9 (died)), (13, 14), (1, 13), (14, 16) (3, 13), (14, 15), (14, 15), (14, 14), (14, 14), (10, 13), (14, 14), (11, 16), (14, 14), and (9, 12).

There were no significant differences in initial pulmonary function when the inhalation patients were compared with either the iv-treated patients in this study or with previously published cases of PCP (p>0.05) (D. L. Coleman et al, *Am Rev Respir Dis* (1984) 129:491–93). The initial chest x-ray was abnormal for all 22 patients.

Three patients (9, 11, and 13) who received inhaled pentamidine were not evaluated due to early discontinuation of the therapy. Of the remaining ten patients, nine had a satisfactory outcome. Three patients (7, 10, and 14) of the nine have been readmitted and treated successfully for *P. carinii* pneumonia at one, three, and two months respectively, following discharge. Of the remaining six (4, 6, 12, 14, 15, and 16), follow-up data is available from one to nine months following discharge, with no recurrence of PCP.

Eight of nine iv-treated patients exhibited a satisfactory outcome. One patient (18) responded satisfactorily, but was changed to dapsone/trimethoprim treatment after ten days because his leukocyte count had decreased to $0.6 \times 10^9$/L (630 cells/mm³). In four patients, follow-up was available from five to six months, with no reported relapses.

By our criteria, major toxicity (neutropenia) was observed in two of ten (20%) evaluable inhalation patients (15 and 17). Both of these patients had also received zidovudine (AZT), and had low pretreatment leukocyte counts ($1.7 \times 10^9$/L (1,770 cells/mm³); and $1.96 \times 10^9$/L (1,960 cells/mm³), respectively). Major toxicity (neutropenia, hepatotoxicity) developed in two of nine (22%) of the iv-treated patients.

Minor toxicity (elevated serum creatinine in three and depressed leukocyte count in one) occurred in four iv-treated patients (2, 8, 18, and 19). One inhalation patient (16) experienced minor toxicity (rash). Reversible bronchospasm associated with the inhalations occurred in five patients (1, 10, 14, 15, and 16), four of whom had a prior history of asthma. Eight of thirteen patients (four of whom also experienced bronchospasm) had mild inhalation-associated cough which did not interfere with therapy.

For patients having three or more pulmonary function studies, lung volumes and diffusing capacity neither improved nor worsened (linear regression, p>0.05) during therapy.

There were no episodes of hypotension or dysglycemia. Among approximately 165 glucose determinations, all were >3.9 mmol/L (70 mg/dL).

Pentamidine concentrations for the inhalation patients are summarized in Table 2. For iv-treated patients, the mean peak plasma concentration during the first infusion was 260±56 ng/mL, and at the completion of the first infusion was 179±185 ng/mL. The maximum plasma concentration during the remainder of therapy ranged from 164 ng/mL on day 5 (patient 3) to 1360 ng/mL on day 14 (patient 19) with a mean of 497±451 ng/mL. Pentamidine concentrations in bronchoalveolar lavage fluid were 10.9±2.9 ng/mL in patient 2 (day 2) and 3.4±0.2 ng/mL in patient 5 (day 6).

Four inhalation patients (4, 6, 12, and 14) had repeat bronchoscopies and lavage. In patients 6, 12, and 14, the mean concentration of pentamidine were 63±22 ng/mL (day 15); 45.7±0.9 ng/mL (day 15); and 3.0±0.5 ng/mL (day 47). In patient 4, the mean concentration of pentamidine was 178±28 ng/mL on day 12, and 5.61±0.78 ng/mL on day 69, following completion of therapy.

Of 13 inhalation patients, 9 (69%) responded satisfactorily, and 4 (31%) were treatment failures. One patient (7.7%) in the inhalation group died in the hospital. Thus, the satisfactory response rate for inhalation therapy is 90%. Eight of nine intravenously-treated patients (89%) responded satisfactorily. These results compare favorably with those previously reported: J. A. Kovacs et al, *Ann Intern Med* (1984) 100:663–71; F. M. Gordin et al, *Ann Intern Med* (1984) 100:495–99; H. W. Haverkos, *Am J Med* (1984) 76:501–08; M. Wharton et al, *Am Rev Respir Dis* (1984) 129:188A. However, three of ten inhalation patients who were successfully treated experienced relapses that may have occurred earlier than expected.

Major toxicity occurred in only 20% of the inhalation group, and 22% of the iv group. However, the patients exhibiting major toxicity in the inhalation group were also receiving AZT, which may have been responsible for the toxic effects observed. Two of 19 (11%) evaluated iv-treated patients required a change of therapy due to toxicity.

TABLE 2

Pentamidine Concentrations In Patients Treated by Inhalation

| | In Lavage Fluid | | | In Plasma | | |
|---|---|---|---|---|---|---|
| Patient | Mean* concentration (ng/mL) | consecutive measures (#) | time before determinations (days) | Conc. on Day 1 † (ng/mL) | Max during treatment ‡ (ng/mL) | Time to max conc. (days) |
| 1 | ND | ND | ND | 3.1 | 6.1 | 5 |
| 4 | 55.3 ± 17.1 | 3 | 1 | 14.7 | 21.8 | 5 |
| 6 | 28.6 ± 10 | 4 | 4 | 16.9 | 7.8 | 5 |
| 7 | 66.8 ± 16 | 3 | 3 | 0.0 | 5.0 | 5 |
| 9 | ND | ND | ND | 7.3 | 13.0 | 2 |
| 10 | 30.6 ± 27.5 | 2 | 14 | 32.8 | 45.4 | 2 |
| 11 | ND | ND | ND | 12.3 | 12.3 | 1 |
| 12 | 16.8 ± 7.3 | 3 | 1 | 2.5 | 6.9 | 2 |
| 13 | ND | ND | ND | 7.4 | 5.0 | 3 |
| 14 | 49.1 ± 22.5 | 4 | 15 | 7.8 | 29.5 | 14 |
| 15 | 149.7 ± 87.2 | 4 | 15 | 35.0 | 11.5 | 2 |
| 16 | ND | ND | ND | 30.9 | 79.2 | 8 |
| 17 | 92.4 ± 53.9 | 4 | 15 | 9.2 | 23.2 | 14 |

*Data are mean ± SD in (N) consecutive lavages
† Peak plasma concentration measured during inhalation on day 1 for patients 1, 4, 6, 7, 15, and 16. Plasma concentration measured at end of inhalation on day 1 for patients 10–14 and 17.
‡ Highest concentration measured during remainder of therapy Serial assessment of the vital capacity, total lung capacity, and diffusing capacity revealed no significant changes during therapy. Some patients experienced pentamidine-related cough, bronchospasm, or temperature elevation. Although no microscopic airway changes have been noted in animals receiving inhaled pentamidine (R. H. Waldman et al, *Am Rev Respir Dis* (1973) 108:1004–06; R. J. Debs et al, *Am Rev Respir Dis* (1987) 135:731–37), hyperreactive airways and mucosal inflammation in humans were still possibilities, as has been shown after other inhalation exposures: J. A. Golden et al, *Am Rev Respir Dis* (1978) 118:287–94. Clinical evidence for such airway damage in humans receiving inhaled pentamidine has not been forthcoming. In patients who receive inhaled pentamidine for the treatment of PCP, cough, bronchospasm, and other signs or symptoms of airway irritation do not persist beyond the treatment period. Further, in repeat bronchoscopy, evidence of mucosal damage has not been observed.

In patients who receive periodic inhalations of pentamidine for the prevention of PCP, signs or symptoms of bronchitis or bronchospasm are not present during the period between inhalations. Repeat bronchoscopy has not revealed evidence of airway mucosal damage.

Aerosol particle size, pentamidine pulmonary deposition and the long term effects of inhaled pentamidine were carefully considered prior to initiating the study. In order to minimize the number of issues that might affect outcome in this study, these factors were not included as variables in the study design.

The Mallinckrodt UltraVent ® nebulizer was chosen because it delivered particles in a size range of about 0.25 to 2.0 μm, which maximizes peripheral distribution into the alveoli. The organism which causes PCP residues in the alveoli. Moreover, the UltraVent nebulizer has previously been used in AIDS patients with PCP and has been demonstrated to deliver aerosol evenly throughout the lungs.

The exact amount of inhaled pentamidine which is deposited in the alveoli is unknown. As indicated above, approximately one third of the dose remains in the nebulizer after inhalation is completed, regardless of the dose size, duration of inhalation, or type of nebulizer used (Respirgard II or UltraVent). Moreover, resuspension of the residue and re-administration does not significantly increase the dose delivered to the patient: about one third remains in the nebulizer. Based on technical specifications provided by Mallinckrodt, we estimate that about 7% of the total dose (e.g., about 21 mg or about 42 mg for a dose of 300 or 600 mg that is placed in the nebulizer to be aerosolized) is delivered to the alveoli.

For treatment of mild to moderate PCP, we have shown that a pentamidine aerosol dose of 4 mg/Kg/day (about 300 mg for a 70 Kg human) provides effective therapy. Higher and lower doses are also effective. For post-exposure prophylaxis, we have shown that administration of a pentamidine aerosol dose of 300 mg by inhalation once monthly results in a 5-fold reduction in the incidence of PCP based on historical controls. Thus, we are able to effect a monthly post-exposure prophylactic treatment with minimal toxicity.

We have demonstrated that a range of doses and types of nebulizers provide effective treatment and prophylaxis of PCP in humans. Concentrations of pentamidine in lavage fluid in the inhalation patients were approximately 10-fold higher than those found in the iv-treated patients. Conversely, very little inhaled pentamidine was absorbed into the systemic circulation: approximately two-thirds of the plasma samples contained no detectable drug. Plasma concentrations in the iv-treated patients were as expected.

EXAMPLE 2

(Delivery of Pentamidine By Aerosol)

This example demonstrates the delivery of pentamidine to the lungs of patients by aerosol. It is shown that aerosolized pentamidine can produce high alveolar concentrations with little systemic uptake, even in patients with diseased lungs.

The system used to generate and deliver the pentamidine aerosol is shown in FIG. 1 (Respirgard II ®, Marquest Medical Products, Inc., Inglewood, Colo.). A compressed oxygen (5–7 L/min at 345 kPa, 50 psi) powered nebulizer produces the aerosol and one-way valves provide for entrainment of room air in patients whose minute ventilation is high, act as a baffle to decrease particle size, and direct expired air to a filter which removes the remaining particles of drug thereby preventing environmental contamination.

The size of pentamidine particles was determined in three locations: (1) immediately distal to the nebulizer at point A in FIG. 1; (2) the stream passing the mouthpiece at point B in FIG. 1; and (3) distal to the exhalation filter at point C in FIG. 1. Particles were sized with a 7 stage Mercer cascade impactor (Intox Products, Albuquerque, N. Mex.). The gas supply was 6 L/min, the sample stream was not dried, and the impactor flow rates were 0.5 L/min. Concentrations of pentamidine from the impactor plates after eluting with 10 mL of sterile water were determined by optical density at 262 nm and compared to standard curves. Results from the average of three determinations at each location were expressed as mass median aerodynamic diameter ±geometric standard deviation (MMAD±GSD). Raabe, *J Aerosol Sci* (1971) Z:289-303.

Pentamidine particle size distal to the nebulizer was 2.38 μm±2.31 (MMAD±GSD) with greater than 20% of the mass of particles being larger than 4 μm. At the mouthpiece, the particle size was 1.42 μm±1.88 (MMAD±GSD) with less than 5% of the mass of particles larger than 4 μm. The mean MMAD of pentamidine in the airstream immediately distal to the nebulizer (point A of FIG. 1) was larger than the airstream passing to the mouthpiece (point B of FIG. 1) ($p<0.002$ by two sample t-test). No pentamidine was found distal to the exhalation filter.

Adult patients having or suspected of having AIDS, and who were hospitalized for a fiberoptic bronchoscopy to evaluate diffuse infiltrates on chest radiographs, were studied. The patients were divided into two groups. The first group consisted of three patients who had been given empiric intravenous pentamidine (4 mg/Kg) prior to bronchoscopy. Two patients had received one dose and the other three doses. Five other patients were given a single exposure to an aerosol of pentamidine for 35-40 min. Three hundred mg of pentamidine isethionate (LyphoMed, Melrose Park, Ill.) dissolved in 6 mL of sterile water was aerosolized until the nebulizer was empty. In the aerosol group, blood samples were drawn prior to and 15, 30, 60, 120, 180 minutes and 24 hours after administration of pentamidine.

Eighteen to 24 hours later both groups underwent fiberoptic bronchoscopy. After inspection of the airways, 3-5 aliquots (20 mL) of normal saline were injected and aspirated from the right middle lobe until at least 40 mL was recovered: C. Broaddus et al, *Ann Intern Med* (1985) 102:742-752. Lavage fluid was centrifuged at 1,000×g for 10 min at 10° C. Pentamidine concentrations in the lavage supernatant, sediment and blood serum were analyzed by methods previously described: R. J. Debs et al, *Am Rev Resp Dis* (1987) 135:731-737; R. J. Debs et al, *Antimicrob Agents & Chemo* (1987) 31:37-41; Lin et al, *J Liquid Chrom* (1986) 9:2035-2046. Briefly, proteins were precipitated with acetonitrile containing hexamidine as an internal standard. After purification with a C-8 bond elute cartridge column (Analytichem, Harbor City, Calif.), pentamidine was separated by high performance liquid chromatography and concentrations were determined by comparison to a standard curve for the drug and to hexamidine as an internal standard. Pentamidine concentrations were expressed as ng/mL of either blood or BAL fluid. The lower limit of sensitivity of the assay was 2-3 ng/mL. Two sample t-test was used to compare groups: p values of $<0.05$ were regarded as significant.

Pentamidine concentrations in BAL supernatant and BAL sediment 18-24 hours after either aerosol or intravenous administration for all patients in both groups are shown in Table 3. Concentrations were greatest in BAL sediment in the aerosol group, exceeding those found in BAL sediment from the intravenous group by 10-100 fold. The mean BAL supernatant concentration in the aerosol group exceeded the sediment concentration in the intravenous group by a factor of more than 2. Of all the serum samples drawn in the aerosol pentamidine group, only one patient in the aerosol group had a measurable amount of pentamidine in serum (13 ng/mL in patient 5 at 30 minutes). All three patients in the intravenous group and 3 of 5 patients in the aerosol group were found to have *P. carinii* pneumonia. All patients infected with *P. carinii* responded to standard therapy with either intravenous pentamidine or TMP-SMX. It was noted that the response to standard therapy by patients in aerosol group was better than the historical average.

This study demonstrated that 18-24 hours after administration, aerosolized pentamidine produces significantly higher concentrations of the drug in the lung than that produced by intravenous injection. Little or no systemic absorption was detectable after aerosol administration. In contrast, mean peak serum pentamidine concentrations using an identical assay in AIDS patients with *P. carinii* receiving a single 4 mg/kg dose of intravenous pentamidine are 612 ng/mL: J. E. Conte Jr. et al, *J Inf Dis* (1986) 154:923-929. Although adverse reactions to pentamidine have not been correlated with its concentration in blood, very low concentrations of the drug in blood probably greatly reduce its effects on organs other than the lungs.

Performing BAL 18-24 hours after administration of the aerosol should have allowed enough time for the drug to have been cleared by the mucocilliary system, thus indicating predominantly alveolar deposition. It is possible, however, that in the presence of lung inflammation and edema, mucocilliary clearance would be slowed and some of the material obtained by lavage was derived from the airways. The finding that concentrations of pentamidine are much greater in BAL sediment than in supernatant is consistent with the drug being taken up by cells within the airspaces. In patients with *P. carinii* pneumonia, BAL sediment is predominantly alveolar macrophages although other cells may have contained pentamidine.

TABLE 3

| Pentamidine Concentrations from Bronchoalveolar Lavage | | |
|---|---|---|
| | BAL supernatant (ng/mL) | BAL sediment (ng/mL) |
| Intravenous Administration: | | |
| Patient 1 | 1.48 | 12.8 |
| Patient 2 | 2.44 | 6.89 |
| Patient 3 | 4.0 | 8.35 |
| Mean ± SEM | 2.64 ± 0.73 | 9.34 ± 1.74 |
| Aerosol Administration: | | |
| Patient 1 | 21.6 | 140 |
| Patient 2 | 23.4 | 141 |
| Patient 3 | 43 | 1057 |
| Patient 4 | 5.1 | 851 |
| Patient 5 | * | 1336 |
| Mean ± SEM | 23.2 ± 7.75 † | 705 ± 242 † |

*unable to measure due to unidentified interfering substance.
† $p<0.05$ compared to intravenous group.

EXAMPLE 3

(Comparison With Other Treatments)

The following example demonstrates that aerosolized pentamidine as the sole therapy for PCP in AIDS patients is effective, and surprisingly eliminates the systemic adverse reactions associated with patients undergoing conventional therapy with parenteral pentamidine, TMP-SMX, or TMP-DPS.

For a 7.5 week period, all patients at San Francisco General Hospital with AIDS who were documented to have a first episode of *P. carinii* pneumonia and who were 18 years or older were evaluated for enrollment in this study. The diagnosis of *P. carinii* pneumonia was based on finding the organism in induced sputum or bronchoalveolar lavage specimens: C. Broaddus et al, (1985), supra; T. D. Bigby et al, *Am Rev Respir Dis* (1986) 133:515-518. All sputum and lavage specimens were also cultured for mycobacteria, fungi and viruses. Patients were excluded for the following reasons: 1) serum creatinine level greater than 2 mg/dL; 2) more than 48 hours of empiric therapy for *P. carinii* pneumonia; or 3) arterial $PO_2$ less than 50 torr breathing ambient air.

Treatment consisted of inhalations of pentamidine aerosol given once daily for 21 days. Treatments were given either in the hospital or outpatient clinic. Six hundred mg of pentamidine isethionate (Pentam ® 300, LyphoMed, Inc., Melrose Park, Ill.) dissolved in 6 mL of sterile water was placed in the nebulizer system described in Example 2. Compressed oxygen, 3445 millibars (50 psi) at 5-7 L/min, was used to power the nebulizer. Pentamidine particle size was 1.42±1.88 (mass median aerodynamic diameter in $\mu m \pm$ geometric standard deviation). The duration of each treatment was approximately 20 min. After therapy, approximately 3 mL of solution remained in the nebulizer and as droplets in the tubing, hence the total dose nebulized was approximately 300 mg.

An initial history and physical examination was performed on all patients, and pertinent examinations were repeated daily. Laboratory studies including complete blood count, platelet count, serum electrolytes, glucose, creatinine, tests of liver function, and serum pentamidine concentrations were performed every 3 days. Chest radiographs, arterial blood gas tensions on ambient air, and urinalysis were performed weekly. Pulmonary function tests were obtained within two days of entry in 13 patients, and within 5 days on 2 patients who were initially unable to cooperate with testing, and were repeated at the time of completion of the study. Failure to respond to aerosol treatment was defined as (i) worsening of symptoms, deterioration of chest radiographs, and arterial blood $PaO_2$ after at least 4 days of aerosol pentamidine therapy, or (ii) lack of improvement after 10 days of therapy. Patients who failed to respond to therapy were switched to intravenous TMP-SMX.

During the study period, 29 patients with AIDS and first episodes of *P. carinii* pneumonia were identified, 15 of whom entered the study. Patients were excluded for the following reasons: 5 patients had more than 48 hours of empiric therapy prior to diagnosis of pneumocystosis, 1 patient declined to participate, and 8 patients had an arterial $PaO_2$ on ambient air of less than 50 torr. The initial values for arterial $PaO_2$, vital capacity and diffusing capacity for carbon monoxide (DLCO) for study patients are shown in Table 4.

Thirteen of 15 patients had subjective and objective improvement during treatment with aerosolized pentamidine. Ten patients had clinical improvement in the first week of therapy, and 3 patients during the second week of therapy. One patient, who was receiving concomitant therapy for tuberculosis, died of progressive respiratory failure; he was changed to intravenous TMP-SMX on day 7 seven and died 6 days later after refusing mechanical ventilation. No autopsy was performed. Another patient was changed to intravenous TMP-SMX because he required mechanical ventilation for acute neurological and respiratory deterioration 20 hours after 1 dose of aerosolized pentamidine. The aerosol delivery system was not designed for use with a mechanical ventilator. This episode appeared unrelated to aerosolized pentamidine and he eventually recovered. He has been subsequently treated with aerosolized pentamidine as suppressive therapy without adverse effects.

All 13 patients treated successfully manifested a marked reduction in dyspnea, respiratory rate and fever. Eleven of the 13 patients showed improvements of their arterial oxygenation and vital capacity. The 2 patients with no improvement in vital capacity and arterial $PO_2$ both had extensive cutaneous Kaposi's sarcoma and a chest radiograph consistent with pulmonary Kaposi's sarcoma. One of these patients had a subsequent bronchoscopy during which airway lesions consistent with Kaposi's sarcoma were seen, and neither bronchoalveolar lavage nor transbronchial biopsy yielded *P. carinii*.

Of the 13 patients treated successfully, 4 had radiographic improvement beginning by the second week of therapy. Five patients showed worsened radiographic infiltrates at one week with subsequent improvement. The remaining 4 patients had worsened radiographic infiltrates or no improvement for the first two weeks of therapy, then improvement at completion of therapy or in follow up radiographs obtained after therapy was concluded.

No adverse systemic reactions (renal, liver and hematologic abnormalities, hypoglycemia or hypotension) were observed in any patient during therapy. Serum pentamidine concentrations were less than 10 ng/mL in 12/14 patients. In 2 patients at the end of therapy, serum pentamidine concentrations were 22 and 32 ng/mL.

The only local adverse reactions associated with therapy was airway irritation. Twelve patients reported coughing with therapy; in 9 patients cough was mild and controlled by pretreatment with inhaled metaproterenol. Coughing was severe in 3 patients, all of whom were smokers, and tolerance to aerosol therapy improved markedly with cessation of smoking in 2 of the 3. The third patient on day 12 of therapy developed increased cough, purulent sputum and fever which was treated with cefuroxime. All symptoms resolved in 2 days and he declined to have further therapy for *P. carinii* pneumonia. He remains well one month post therapy and denies dyspnea. The only other antimicrobial agent used in this group of patients was Amphotericin B in 3 patients with central nervous system cryptococcosus.

Neither clinical nor spirometric evidence of airway obstruction occurred. The FEV1/FVC ratio was no different before and after a single treatment in the first 4 patients. Furthermore, there was no change in the FEV1/FVC ratio prior to and after completion of therapy; 76.1±12.2% (mean±1 SD), on initial testing and 79.9±15.8% at the end of therapy.

The 13 patients who successfully completed therapy were followed for 2-4 months. No patient presented evidence of relapse.

This study shows that aerosolized pentamidine is a safe and effective treatment for mild to moderate *P. carinii* pneumonia in patients with AIDS. The observed 87% overall efficacy rate (95% confidence limits, 58% to 98%) is equal to or better than the results with TMP-SMX and parenteral pentamidine as well as TMP-DPS. M. Wharton et al, *Ann Intern Med* (1986) 105:37-44; G. S. Leoung et al, Id., 105:45-48. The criteria for entry to the current study were similar to previous studies. As shown in Table 4, initial arterial PaO2, percent predicted vital capacity, and DLCO in the patients treated with aerosolized pentamidine were equal to or lower than the values found in the prior studies (M. Wharton et al, supra; G. S. Leoung et al, supra). In addition, the net improvement in arterial oxygenation and vital capacity was similar among the patients from all three studies. These data indicate that the patients given aerosolized pentamidine were as ill and had as much improvement as those treated with TMP-SMX, parenteral pentamidine or TMP-DPS.

The elimination of adverse systemic reactions is the most striking observation of the study in view of the 50% rate of severe reactions with parenteral pentamidine, TMP-SMX and 13-25% rate of severe toxicity requiring change of therapy with TMP-DPS. M. Wharton et al, supra; G. S. Leoung et al, supra; J. A. Kovacs et al, *Ann Intern Med* (1984) 100:663-671; F. M. Gordin et al, Id., 100:495-499; Medina et al, Proceedings of the III Int'l Conf. on AIDS, p. 208 (Washington, D.C. 1987). The only adverse reaction to aerosolized pentamidine was coughing. Coughing was most severe in patients who were cigarette smokers and continued to smoke during the study. Clinical bronchospasm was not seen, and FEV1/FVC ratios pre and post therapy were not significantly altered. Airway irritation was minimized because the small particle size produced by the nebulizer system employed favors alveolar rather than airway deposition. Aerosol devices that produce larger particles cause more irritation; for instance, when the baffle from the device was removed, thereby increasing the number of larger particles, most subjects began coughing within a few breaths.

TABLE 4

Comparison of Aerosolized Pentamidine With Other Therapies for PCP

|  | Aero. Pent n = 15 | TMP-DPS* n = 15 | Par. Pent ǂ n = 0 | TMP-SMX ǂ n = 20 |
|---|---|---|---|---|
| Pre therapy | | | | |
| PaO2 (torr) | 67.9 | 74.0 ¶¶ | 69.3 | 63.9 |
| Vital Capacity | 50.8 † | 52.3 ¶ | 70 | 60 |
| DLCO | 64.9 † | 59.8 ¶ | 59.0 | 58.0 |
| Post Therapy | | | | |
| PaO2 (torr) | 80.1 ¶ | 88.7** | 87.2 | 84.9 |
| Vital Capacity | 61.8 ¶ | 78 ¶ | 80 | 76 |
| DLCO | 61.7 ¶ | 62.3 ¶ | 62 | 63 |
| Successful Treatment w/o Change n (%) | 13(86) | 13(86) | 8(40) | 5(20) |
| Successful Treatment W/ Change n (%) | 14(93) | 15(100) | 19(95) | 15(75) |
| Toxicity Req Change | 0(0) | 2(13) | 11(55) | 10(50) |

TABLE 4-continued

Comparison of Aerosolized Pentamidine With Other Therapies for PCP

|  | Aero. Pent n = 15 | TMP-DPS* n = 15 | Par. Pent n = 0 | TMP-SMX n = 20 |
|---|---|---|---|---|
| of Therapy n (%) | | | | |

*G. S. Leoung et al, *Ann Intern Med* (1986) 105:45-48.
ǂM. Wharton et al, *Ann Intern Med* (1986) 105:37-44.
† 14 patients tested.
¶¶ Only 12 patients tested.
¶ Includes only patients (n = 13) who had determination done both at beginning and end of therapy.
**Only 8 patients tested.
(DLCO diffusion capacity for carbon monoxide.)
"Aero" = aerosolized pentamidine; "Par." = parenteral pentamidine.

All of the patients in this study received at least some of their treatments as outpatients with 3 receiving their entire course on an outpatient basis. An initial period of hospitalization to deal with the multiplicity of medical and social problems confronting these patients was usually needed after which outpatient therapy was begun. The average hospital stay in the patients who were treated successfully was 8 days and several patients could have gone home earlier but remained hospitalized for other AIDS related conditions. The decrease in length of hospitalization and in the number of laboratory tests needed for monitoring for adverse reactions offer potential cost savings.

EXAMPLE 4

(Aerosolized Pentamidine in Sensitive Patients)

This example demonstrates that aerosolized pentamidine is an effective nontoxic therapy for PCP in AIDS patients with prior or concurrent severe adverse reactions to TMP-SMX or parenteral pentamidine.

During a 10-½ month period, all AIDS patients at San Francisco General Hospital who (i) were suffering PCP, (ii) were 18 years or older, (iii) had received therapy with either TMP-SMX or parental pentamidine isethionate or a combination thereof for a total of less than fourteen days, and (iv) developed or had a past history of significant adverse reaction to both agents were eligible for compassionate use aerosolized pentamidine. The initial diagnosis of *P. carinii* pneumonia was based on finding the organism in induced sputum or bronchoalveolar lavage specimens.

Treatment consisted of inhalation of pentamidine aerosol once daily for a total of 21 days of aerosolized and prior therapy, unless hypoxia, or dyspnea and fever had resolved, in which case the therapy was discontinued earlier at the option of the attending physicians. Treatment was as described in Example 3.

All patients were examined daily and laboratory studies, including complete blood count, platelet count, serum electrolytes, glucose, creatinine tests of liver function, were done near the time of initiation and every three days or more if clinically indicated. Chest radiographs and arterial blood gas tensions were obtained as clinically indicated. Failure of aerosol pentamidine therapy was defined as either (a) worsening of respiratory symptoms, and deterioration of chest radiographs and arterial PaO2 while on therapy, or (b) development or worsening of severe adverse reaction as defined below:

| Neutropenia | ≦750 PMN/µL |
|---|---|
| Thrombocytopenia | ≦40,000/µL |

-continued

| | |
|---|---|
| Rise in creatinine | ≧3.0 mg/dL |
| Liver function abnormalities | SGOT or SGPT ≧5x normal |
| Hypoglycemia | <50 mg/dL |
| Rash | with fever or mucositis |
| Cough | cough or bronchospasm uncontrolled by metaproterenol preventing >50% of delivered dose for greater than 2 days |

Of approximately 240 cases of *P. carinii* pneumonia at San Francisco General Hospital over the duration of the study, 10 patients met the criteria and consented for compassionate aerosol pentamidine use.

Aerosolized pentamidine therapy ranged from 4 to 17 days. All patients successfully completed therapy. In addition, none of the patients were hypoxic or febrile, all had improvement in dyspnea, and all had current or subsequent chest radiographs indicating roentrographic improvement of infiltrates. No patient developed any severe adverse reactions as defined in the treatment protocol.

EXAMPLE 5

(Prevention of *Pneumocystis carinii* Pneumonia)

This example demonstrates that aerosolized pentamidine is an effective post-exposure prophylactic measure for preventing PCP in patients at risk for this disease due to immunodeficiency.

We have treated 103 patients judged to be at risk for PCP (85.5% with AIDS, 14.5% with ARC) using 300 mg of aerosolized pentamidine once per month, administered using a Mallinckrodt UltraVent® nebulizer. Within 30 days of initiation of prophylaxis, ten patients were omitted due to treatment (9) or relapse (1). Results for the remaining 93 patients are summarized in Table 5 below. Of the 93 patients, 48 had had at least one previous episode of PCP. Two-thirds of the patients were taking AZT at the onset and throughout the duration of the post-exposure prophylaxis. The median and maximum duration of treatment at the time of analysis was 3.1 and 5.2 months.

TABLE 5

| Prophylactic Use of Aerosolized Pentamidine | | |
|---|---|---|
| Prophylaxis Time (months) | Percent Alive & Free of Relapse | Standard Error |
| 0.0 | 100.0 | |
| 2.3 | 98.57 | 1.42 |
| 2.5 | 97.12 | 2.01 |
| 2.9 | 95.53 | 2.53 |
| 3.0 | 93.85 | 2.99 |
| 3.1 | 92.08 | 3.42 |
| 3.7 | 89.78 | 4.03 |
| 5.2 | 79.81 | 7.55 |

In patients who had a single prior episode of PCP, inhaled pentamidine post-exposure prophylaxis delayed relapse by at least 5 months and decreased the number of observed cases from 10, based on 132 historical controls, to 3 in this cohort (p<0.01). No major pentamidine-related toxicity has been observed in these patients.

EXAMPLE 6

(Prevention of *Pneumocystis carinii* Pneumonia)

This example illustrates prevention of PCP using different dosages and regimens.

A total of 438 participants were selected on the basis of seropositivity for HIV, and were stratified on the basis of (i) prior PCP (n=250), (ii) Kaposi's sarcoma (n=59), or (iii) ARC (n=129). These participants were randomized into three experimental groups which received pentamidine isethionate aerosolized and administered as in Example 1: group (a) received 30 mg once every two weeks; group (b) received 150 mg once every two weeks; and group (c) received 300 mg once every four weeks.

The distribution of the patient groups i-iii over the experimental groups a-c was as follows:

| | | Distribution: | | |
|---|---|---|---|---|
| | | Group a | Group b | Group c |
| i | prior PCP | 79 (77) | 81 (77) | 85 (82) |
| ii | Kaposi's | 19 (17) | 20 (20) | 18 (18) |
| iii | ARC | 42 (39) | 43 (37) | 43 (42) |

Number of participants receiving at least one treatment is reported in parentheses.

The following dose-related side effects were reported:

| | Side Effects: | | |
|---|---|---|---|
| | Group a | Group b | Group c |
| Cough | 25% | 34% | 34% |
| Wheezing | 10% | 14% | 14% |
| Metallic Taste | 11% | 16% | 20% |

Participants experiencing cough or wheezing were administered a bronchodilator, and administration continued (uninterrupted administration of pentamidine is not essential). Participants experiencing a metallic taste were allowed to drink liquids, and administration was continued.

A total of 37 of the participants withdrew from the study after receiving at least one treatment, due to physician or subject preference, leaving the area, illness not due to PCP, and other reasons. There were no withdrawals due to toxicity. A total of 409 participants received at least one treatment. The following incidence of PCP relapse was reported after a mean length of treatment of six months:

| | | PCP Events: | | |
|---|---|---|---|---|
| | | Group a | Group b | Group c |
| i | prior PCP | 6* (1) | 5* (3) | 3≠ (1) |
| ii | Kaposi's | 0 | 1 | 0 |
| iii | ARC | 2* (1) | 0 | 0 |

Parenthetical figures are deaths due to PCP
* = One patient in group received <3 treatments
≠ = Two patients received <3 treatments.

Thus, of the 372 participants who remained in the study after receiving at least one treatment, only 17 experienced relapse, for a rate of 4.6%. Of the participants receiving at least three treatments, the rate was only 3.2%. The mortality rate was 1.6%. For the 236 participants in group i (prior PCP) who remained in the study, the relapse rate was 5.9% for those receiving at least one treatment, and 4.2% for those receiving three or more treatments. In contrast, a study of historical case controls indicates a relapse rate of 24.3% (37/152). A study of 74 consecutive patients with first episode PCP at San Francisco General Hospital concluded that the probability of a second acute PCP episode to be 18% after six months. These results indicate that administration of aerosolized pentamidine following the method of the invention was effective in reducing and preventing the incidence of PCP in subjects at risk for clinically manifest infection.

EXAMPLE 7

One hundred fifty-one participants judged to be at risk for development of PCP (42% AIDS, 58% ARC) were entered into a randomized trial to investigate administration of aerosolized pentamidine at 300 mg twice per month versus 600 mg once per month. Pentamidine was administered over a period of 30 minutes to participants in a seated position using an UltraVent® nebulizer. Five patients who developed PCP within 28 days were not evaluated. One hundred (66%) of the patients were concurrently receiving AZT, and 42 (28%) had experienced one prior episode of PCP. Eighty (53%) were receiving aerosolized pentamidine prophylaxis prior to entry into the study.

At a mean duration of 10.6 months at 600 mg aerosolized pentamidine, 10 patients (6.8%) developed PCP. The attack rates of PCP in the 300 mg group (5.6%) and the 600 mg group (8.1%) were not significantly different. When compared with a similar group of patients receiving 300 mg once per month in a previous study, the attack rate at 6.38 months was reduced from 18% to 3% ($p<0.01$). Prophylaxis was discontinued in one patient due to bronchospasm. Twelve of the 146 (8%) evaluable patients died; 3 (2%) deaths were associated with PCP and 9 (6%) were due to other causes.

EXAMPLE 8

(Clinical Trial)

A prospective, randomized, unblinded comparison of a low dose to two higher dosage regimens of aerosolized pentamidine was conducted for 18 months. Eligible participants were 18 years of age or older, gave informed consent, and met criteria of one of three randomization strata: 1) at least 1 prior episode of PCP; 2) Kaposi's Sarcoma without prior PCP; or 3) other AIDS defining infections or cancers without prior PCP or AIDS-related complex (ARC) with either oral thrush or hairy leukoplakia. Participants were excluded with history of sever asthma, anaphylactic reaction to pentamidine, prior aerosolized pentamidine prophylaxis, or current use (within two weeks) of dapsone, trimethoprim/sulfamethoxazole, pyrimethamine/sulfadoxin, pyrimethamine with sulfadizaine, parenteral pentamidine or difluoromethylornithine. Participants were enrolled in one of 13 treatment centers located in the San Francisco Bay area. Health care providers enrolled participants by contacting the data center which provided a randomization number and treatment dose: 30 mg every two weeks, 150 mg every two weeks, or 300 mg every four weeks. Each strata had a separate set of sealed cards with treatments assigned in random blocks of three and six.

Pentamidine isethionate was dissolved in 6 mL sterile water and administered over 35–40 minutes using a Respirgard II nebulizer either at a flow rate of 5–7 L/min from a pressure compensated flowmeter attached to a 50 psi air source, or at a pressure between 22–25 psi from a BUNN BA 400 air compressor (John Bunn Co., Tonawanda, N.Y.). Each treatment was supervised by a respiratory therapist who noted any immediate adverse effects and administered a bronchodilator if needed for severe coughing or bronchospasm.

Each participant was follows from randomization until death or for 18 months. Six participants were lost to follow-up after 12 months. Participants were questioned at baseline and at each visit about concomitant medications, intercurrent illnesses, and symptoms. Information from participants, their physicians, hospital records, microbiology departments, and county health departments were used to determine status.

PCP was defined as an episode of pneumonitis. "Confirmed PCP" is the observation of the organism from induced sputum or bronchoscopy with clinical illness characteristic of PCP. "Unconfirmed" episodes lacked histological confirmation, but were clinically consistent with acute PCP with response to therapy or death, where no other etiology was found. Episodes with a normal bronchoscopy were not considered unconfirmed episodes of PCP. Participants were defined as ineligible if they did not take the study drug, were taking a prohibited medication at randomization ($n=17$), had received prior pentamidine prophylaxis ($n=10$), were HIV negative ($n=1$), or had an acute attack or death in the first 28 days of follow-up ($n=14$). An episode of PCP was considered to have occurred "on study drug" if the episode occurred within 60 days of or before withdrawal from study drugs.

"Intention to treat" analysis included all participants, eligible or not, and whether occurring on study medications or not. While this analysis will generally underestimate efficacy, it protects against possible bias created by exclusion of participants, and differential study drug withdrawal.

Analysis of participants "on study drug" was limited to those eligible. PCP episodes which occurred 60 days or more after the last dose of study drug were not counted, and those participants were censored on the day of last treatment. "Confirmed on study drug" analyses censors the participants at the onset of an unconfirmed episode.

The hypothesis was tested between each of the dose pairs with a Bonferroni adjustment of the p value to account for three planned contrasts (30 vs. 150, 30 vs. 300, 150 vs. 300). Two interim analyses were performed using the method of P. C. O'Brien et al, (*Biometrics* (1979) 35:549–56) with p values=0.0006, 0.015, and 0.047. Thus, the Bonferroni adjusted p value for significance of contrasts between the two higher doses to the lower dose=0.024. The differences between doses was tested using the log rank statistic of the Kaplan-Meier product limit estimates using Proc Lifetest of SAS. In addition, the Cox proportional hazards regression model was performed with BMDP (L2) to estimate the effects of covariates.

Four hundred forty-one individuals were randomized. Thirty-three were never treated with the study drug. Of the 408 study participants treated, 237 were in the prior PCP stratum, 55 in the Kaposi's sarcoma stratum, and 116 in the other HIV-related conditions stratum. (Table 6). All but three participants were men, ranging in age from 20 to 62 years (mean 37.7 years). HIV-related conditions included Kaposi's sarcoma ($n=107$), disseminated Mycobacterium avium complex infection ($n=22$), cryptococcal meningitis ($n=17$), and CNS toxoplasmosis ($n=8$). These conditions were evenly distributed across randomized doses, as were lymphadenopathy, oral candidiasis, hairy leukoplakia, and herpes virus infections. Participants with a history of PCP started the study on average 135 days after the most recent episode (range 13–1011, median 74 days). This interval did not significantly differ across the randomized groups.

Baseline CD4 cell counts were collected from 93 participants in the other HIV stratum and 35 participants in the Kaposi's sarcoma stratum. The CD4 cell counts for these participants ranged from 8 to 676 (mean=160.8/mm$^3$, median=128/mm$^3$) and did not significantly differ across randomized groups.

The most frequent concomitant medication was zidovudine, taken by 52% of participants at study initiation. Another 20% began zidovudine therapy during the study. Acyclovir (n=187), clotrimazole (n=59), and ketoconazole (n=53) were also frequent concomitant or past medications. Previous drugs for prophylaxis were reported by 61 participants. There were no differences across the 3 dosage groups for the number of participants taking concurrent medications.

TABLE 6

| | Participants at Study Entry | | | |
|---|---|---|---|---|
| | 30 mg (n = 135) | 150 mg (n = 134) | 300 mg (n = 139) | p* |
| Strata (n) | | | | |
| Prior PCP | 79 | 78 | 80 | |
| Kaposi's Sarcoma | 17 | 22 | 16 | |
| Other HIV | 39 | 34 | 43 | .71 |
| Related HIV Conditions (%) | | | | |
| Prior PCP once | 47.4 | 45.5 | 50.4 | .72 |
| Prior PCP ≧ twice | 11.1 | 12.7 | 7.2 | .31 |
| Kaposi's Sarcoma | 26.7 | 25.4 | 26.6 | .96 |
| Mycobacterium Avium | 5.9 | 5.2 | 5.0 | .94 |
| Cryptococcal meningitis | 2.2 | 3.7 | 6.5 | .20 |
| CNS Toxoplasmosis | 0.7 | 3.0 | 2.2 | .41 |
| Baseline Medications (%) | | | | |
| Zidovudine Use | 53.3 | 53.7 | 50.4 | .83 |
| Acyclovir Use | 23.0 | 21.6 | 23.7 | .92 |
| Chemotherapy | 8.1 | 5.2 | 4.3 | .37 |
| Prior Sulfa Prophylaxis | 5.9 | 2.2 | 2.9 | .23 |
| Ketoconazole | 3.7 | 3.0 | 4.3 | .84 |

*Chi square or Fisher's Exact for Proportions

The study duration was 18 months. One hundred six participants (26%) completed the study without reaching a study endpoint. Of the remainder, the first endpoint reached was treatment discontinuation (n=184), *P. carinii* pneumonia (n=75), and death (n=43). The 30 mg dosage arm had the fewest number of completing participants, primarily due to a greater number of PCP events (Table 7).

TABLE 7

| Participant Outcomes at Study End | | | |
|---|---|---|---|
| | 30 mg | 150 mg | 300 mg |
| PCP, Confirmed | 32 | 28 | 16 |
| Unconfirmed | 9 | 4 | 12 |
| Died, Not due to PCP | 51 | 47 | 46 |
| Due to PCP | 5 | 6 | 5 |
| Completed without Endpoint | 26 | 38 | 42 |
| Withdrew (total) | 62 | 56 | 68 |
| Adverse Effects | 2 | 11 | 10 |
| to increase dose | 22 | 3 | 0 |
| to decrease dose | 0 | 1 | 2 |
| Moved | 8 | 4 | 8 |
| Protocol Violation* | 13 | 19 | 27 |
| Respiratory Side Effects: | | | |
| Used Bronchodilators | 7.5% | 14.% | 20.% |
| Significant Cough | 31.% | 40.% | 38.% |

TABLE 7-continued

| Participant Outcomes at Study End | | | |
|---|---|---|---|
| | 30 mg | 150 mg | 300 mg |
| Treatments stopped due to cough | 0% | 0.2% | 0.7% |
| Pneumothorax | | | |
| Known etiology | 5 | 5 | 3 |
| Spontaneous | 2 | 3 | 3 |
| Extrapulmonary Pneumocystis | 0 | 1 | 0 |

*Taking medication prohibited by protocol, or multiple month gaps in treatment

One hundred-one PCP episodes were documented during the study, including 26 that occurred after treatment discontinuation. Seventy-eight occurred in the prior PCP stratum, 8 in the KS stratum, and 15 in the Other HIV stratum. Twenty-five PCP events were not histologically confirmed.

Death occurred in 160 participants, 117 after reaching another study endpoint. Nineteen deaths occurred due to PCP. Sixteen were associated with the first subsequent episode of PCP after the start of the study, and 3 with second or third episodes.

One hundred eighty-six participants withdrew from the study protocol, but were followed to the end of the trial. Six were lost to follow-up. The most common reasons for discontinuation were noncompliance and other protocol violations, dose increase, and dose decrease. Noncompliance was defined as a treatment gap of more than 2 months, or taking a medication prohibited by the protocol.

The duration of aerosolized pentamidine treatment for all participants ranged from 1 to 536 days, with a median of 212 days. Compliance was measured as a percentage of scheduled treatments received before a study endpoint. Average compliance with treatment ranged from 91% in the 150 mg group to 95% in the 300 mg group.

The 300 mg dosage arm experienced the fewest PCP episodes whether analyzed with the "intention to treat" or "on study drug events" rule (Table 8). Kaplan-Meier plots of the proportion PCP-free "on study drug" shows a widening difference in effectiveness with time comparing the 30 mg to the 300 mg dosage arm. The log rank statistics comparing the 30 mg to the 300 mg arms are statistically significant for all levels of analysis.

The Cox proportional hazard regression model estimated the dose-response for aerosolized pentamidine while controlling for baseline covariates (Table 8). Covariates included study strata, treatment center, AZT use and time since prior PCP. The 300 mg group had a significantly lower hazard of PCP with either the "intention to treat" or "confirmed on study drug" analysis rule. The same results were obtained in the prior PCP stratum alone. The 150 mg dosage arm was consistently less effective than 300 mg when compared with the 30 mg arm, although never statistically significantly different from 300 mg.

TABLE 8

| Study Endpoints by Dose & Eligibility | | | | |
|---|---|---|---|---|
| | 30 mg | 150 mg | 300 mg | p* |
| All Strata: | | | | |
| Intention to Treat | | | | |
| All PCP | | | | |
| PCP | 41 | 32 | 28 | |
| No PCP | 94 | 102 | 111 | .02 |
| Eligible participants | | | | |
| PCP within 60 Days | | | | |

TABLE 8-continued

Study Endpoints by Dose & Eligibility

|  | 30 mg | 150 mg | 300 mg | p* |
|---|---|---|---|---|
| PCP | 28 | 18 | 16 | |
| No PCP | 89 | 102 | 113 | .004 |
| Eligible participants Confirmed PCP within 60 Days | | | | |
| PCP | 22 | 16 | 8 | |
| No PCP | 95 | 104 | 121 | .0008 |
| Prior PCP Strata: | | | | |
| Intention to Treat | | | | |
| All PCP | | | | |
| PCP | 33 | 24 | 21 | |
| No PCP | 46 | 54 | 59 | .02 |
| Eligible Participants | | | | |
| PCP within 60 Days | | | | |
| PCP | 25 | 16 | 14 | |
| No PCP | 42 | 51 | 60 | .006 |
| Eligible Participants Confirmed PCP within 60 Days | | | | |
| PCP | 20 | 14 | 8 | |
| No PCP | 47 | 53 | 66 | .002 |

*Log Rank Statistic comparing Kaplan Meier curves of the 30 mg vs. 300 mg dosage arm.

AZT use independently reduced PCP risk two-fold in the Cox models. The combined effects of zidovudine and aerosolized pentamidine in the model are multiplicative and indicate better protection with both than from either drug alone. Thus, it is presently preferred to administer AZT to patients undergoing aerosolized pentamidine therapy for PCP. Increased time from prior PCP also independently predicted increased risk in the Cox model. Participants starting therapy within 3 months had less than half the hazard of PCP compared with those starting later, suggesting improved efficacy with the earlier treatment. PCP relapses occurred at a median of 240 days for participants starting prophylaxis within 3 months, versus 143 days for those starting with a longer interval since the prior episode.

A CD4 count less than 200 was associated with a 2.6 relative risk (95% confidence interval 0.62-11.2) for PCP in participants without prior PCP. Two of the 39 participants with initial CD4 counts greater than 200 developed PCP (5.1%), compared with 12 of the 89 participants (13%) with initial CD4 counts less than 200.

All cause mortality did not significantly differ between the three treatment arms. There was litter power to detect a dose-response for PCP mortality since PCP was the cause of death in only 11.9% of all deaths (19 of 160). The most frequent cause of death was opportunistic infection other than P. carinii, which accounted for 41% of all deaths. All cause mortality was higher in the prior PCP stratum (53%) than in the Kaposi's sarcoma (36%) or other HIV (13%) strata. Participants who had never taken zidovudine had a significantly higher mortality (67%) than participants who had (28%). The case fatality rate from the first acute episode of PCP after randomization was 15.8% (16 of 101 PCP episodes). There were no significant differences between the dosage arms. At autopsy, one participants was found to have calcified granulomas in the liver and spleen which contained P. carinii. He had died after a wasting syndrome, and the contribution of the extrapulmonary pneumocystis was not clear.

Respiratory therapists reported that 36% of participants had significant coughing and 11% reported wheezing during a treatment. The prior PCP stratum participants reported significantly more coughing (43%). Wheezing occurred in significantly more participants in the 150 mg and 300 mg dosage arms. Although cough during aerosol therapy occurred often, it only interrupted 0.5% and ended 0.3% of treatments. Fourteen percent of the participants used bronchodilators during treatment, on one or more occasions. Use was more common in the 150 mg and 300 mg dosage arms. Twenty-three participants (5.6%) discontinued study drugs due to adverse experiences. Eight (2.0%) were due to adverse experiences associated with treatment: 4 with bronchospasm and cough; 1 each with dizziness and light-headedness; upper respiratory complaints and lip numbness; diaphoresis, unsteadiness, and nausea; and gagging. One participant had a rash. One participant stopped study medications due to interstitial pneumonitis. The cause of the interstitial pneumonitis is unknown, but this condition appeared to have been present before the start of the aerosolized pentamidine therapy. Ten participants withdrew because of concurrent illnesses or infections related to HIV, and four withdrew after pneumothoraces.

Pneumothorax occurred in 21 participants while on aerosolized pentamidine; in 2 participants more than 4 months after last treatment. Eight were spontaneous, 3 caused by invasive procedures, 5 associated with acute PCP, and 3 with bacterial pneumonia. There was no difference in occurrence across treatment arms. No pneumothorax occurred during a treatment.

The three dosage arms were compared by the log rank statistic of the Kaplan-Meier curves and with Cox proportional hazard regression models. In the Kaplan-Meier analyses of time to PCP occurrence, 300 mg of aerosolized pentamidine given every 4 weeks was consistently superior to 30 mg of aerosolized pentamidine given every 2 weeks. The 150 mg arm was superior to the 30 mg arm but less so than the 300 mg arm. The Cox relative hazard of 30 mg for "on study drugs" events was 1.7 for 150 mg, and 3.9 for 300 mg (Table 9). The greatest risk for PCP occurs in patients with a prior episode (secondary prophylaxis). The same result, of the superiority of the 300 mg, was also observed in this stratum alone. A significant dose response was not found for primary prophylaxis in the two other strata, possibly because the small number of events did not provide adequate resolution. The Cox model for "intention to treat" estimated the risk in the primary prophylaxis strata to be 0.26 to 0.33 compared with the risk of the secondary prophylaxis stratum. Both epidemiologic studies and our results show an increased risk for primary prophylaxis participants with CD4 counts below 200 cells/$mm^3$.

While the incidence of pulmonary side effects was high, their severity was low. Only 2.0% of participants withdrew from the study regimen due to side effects attributed to aerosolized pentamidine.

TABLE 9

Relative Hazard of PCP: Cox Regression Estimates

|  | 30 vs. 150 | 30 vs 300 |
|---|---|---|
| All Strata: | | |
| Intention to Treat: | | |
| Pentamidine Dose | 1.21 | 1.78 ‡ |
| Zidovudine (ever) | 2.53* | 2.19 † |
| Kaposi's Sarcoma | .26 † | .32 † |
| Other HIV Conditions | .33 † | .26 ‡ |
| Confirmed PCP on Study Drug: | | |
| Pentamidine Dose | 1.71 | 3.86* |
| Zidovudine (ever) | 1.70 | 2.00 |
| Kaposi's Sarcoma | .18 ± | .07 † |

TABLE 9-continued

| Relative Hazard of PCP: Cox Regression Estimates | | |
|---|---|---|
| | 30 vs. 150 | 30 vs 300 |
| Other HIV Conditions | .11† | .05 † |
| Prior PCP Strata: | | |
| Intention to Treat: | | |
| Pentamidine Dose | 1.40 | 2.11 † |
| Zidovudine (ever) | 2.01 ‡ | 1.79 |
| <3 months since PCP | 1.39 | 1.67 |
| Confirmed PCP on Study Drug: | | |
| Pentamidine Dose | 2.10 ‡ | 4.57* |
| Zidovudine (ever) | 1.66 | 1.61 |
| <3 months since PCP | 2.46 ‡ | 2.30 ‡ |

*p<.001
† - p<.01
‡ - p<.05

While the present invention has been described above by way of illustrative examples, it is understood that the invention is not limited thereby, and is defined by the scope of the appended claims.

What is claimed:

1. A method for prevention of Pneumonia caused by *Pneumocystis carinii* in human patients, by inhalation of an aerosolized pentamidine or salt thereof, said salt chosen from the group consisting of pentamidine isethionate, pentamidine glutamate, pentamidine lactate and pentamidine hydrochloride, and by delivery of said aerosolized pentamidine salt into the patients' alveoli in an amount which suppresses the growth of *Pneumocystis carinii* organisms improves patients' arterial oxygenation and vital capacity and reduces dyspnea and respiratory rate, wherein said method comprises the steps of:
   (a) preparing a solution consisting of about 300 mg of said pentamidine salt in sterile water;
   (b) nebulizing said pentamidine salt solution into particles having a mean particle diameter from about 0.25 to about 5 μm using a nebulizer which consists essentially of:
     (ii) a tube providing an oxygen flow into the nebulizer;
     (ii) a nebulizer container holding the pentamidine solution for generation of aerosolized particles in a conduit;
     (iii) the conduit;
     (iv) a mouthpiece;
     (v) a one way valve having a baffle for reducing larger particles to the particles having a mean diameter from about 0.25 to about 5 μm;
     (vi) a one way valve leading to the particle filter for removal of residual pentamidine during exhalation; and
   (c) administering said pentamidine salt nebulized in step (b) for 15-60 minutes to patients once in two to four weeks.

2. The method of claim 1 wherein oxygen flows through the tube at a rate of 5-7 liters per minute into the nebulizer container filled with the pentamidine salt solution and aerosolizes pentamidine and generates particles between 0.5 to 5 microns in conduit;
   wherein the patient being treated draws on the mouthpiece drawing the air through the one-way valve, and the airstream entrains the pentamidine particles in the conduit;
   wherein the airstream containing the pentamidine aerosol particles passes around the baffle of the one-way valve which baffle reduces the particles having a mean particle size larger than 2 μm to the particles having a mean diameter in a range from about 1 to about 2 μm microns; and
   wherein the patient draws the nebulized particles through the mouthpiece into the lungs.

3. A method for prophylaxis of Pneumonia caused by *Pneumocystis carinii* in human patients by inhalation of an aerosolized pentamidine isethionate, and delivery of said aerosolized pentamidine isethionate into the patients' alveoli in an amount which suppresses and improves patient's arterial oxygenation and vital capacity and reduces dyspnea and respiratory rate, comprising the steps of:
   (a) preparing a solution consisting of about 300 mg of said pentamidine isethionate in sterile water;
   (b) nebulizing said pentamidine isethionate solution into particles having sizes predominantly from about 0.25 to about 5 μm using a nebulizer which consists essentially of:
     (i) a tube providing an oxygen flow into the nebulizer;
     (ii) a nebulizer container holding the pentamidine isethionate solution for generation of aerosolized particles in a conduit;
     (iii) the conduit;
     (iv) a mouthpiece;
     (v) a one way valve having a baffle for reducing larger particles to the particles having a mean diameter from 0.25 to 5 μm;
     (vi) a one way valve leading to particle filter for removal of residual pentamidine during exhalation; and
   (c) administering said pentamidine isethionate nebulized in step (b) for 15-45 minutes to patients once every three to four weeks.

4. The method of claim 3 wherein oxygen flows through the tube at a rate of 5-7 liters per minute into the nebulizer container filled with the pentamidine isethionate solution and aerosolizes pentamidine and generates particles between about 0.5 to about 5 microns in conduit;
   wherein the patient being treated draws on the mouthpiece drawing the air through the one-way valve, and the airstream entrains the pentamidine particles in the conduit;
   wherein the airstream containing the pentamidine isethionate aerosol passes around the baffle of the one-way valve which baffle reduces the particles having a mean particle size larger than about 2 μm to the particles having a mean diameter in the range from about 1 to about 2 μm;
   wherein the patient draws the nebulized particles through the mouthpiece into the lungs.

5. The method of claim 4 wherein 300 mg of pentamidine isethionate is dissolved in around 6 ml of sterile water and nebulized.

6. The method of claim 4 wherein the aerosolized pentamidine is administered once in three weeks.

7. A method for prophylaxis of Pneumonia caused by *Pneumocystis carinii* in human patients by inhalation of an aerosolized pentamidine isethionate, and delivery of said aerosolized pentamidine isethionate into the alveoli in an amount which suppresses the growth of the *Pneumocystis carinii* organisms, comprising the steps of:
   (a) preparing a solution consisting of about 300 mg of said pentamidine isethionate in 6 ml of sterile water;
   (b) nebulizing said pentamidine isethionate solution into particles having a mean particles diameter from about 0.25 to about 5 μm using a nebulizer which consists essentially of:
(i) a tube providing an oxygen flow into the nebulizer;
(ii) a nebulizer container holding the pentamidine isethionate solution of step (a) for generation of aerosolized particles in a conduit;
(iii) the conduit;
(iv) a mouthpiece;
(v) a one way valve having a baffle for reducing larger particle to particles having a mean diameter from about 0.25 to about 5 μm;
(vi) a one way valve leading to particle filter for removal of residual pentamidine during exhalation; and
(c) administering said pentamidine isethionate nebulized in step (b) for 15-45 minutes to the patients daily for 4-21 days;

wherein oxygen flows through the tube at a rate of 5-7 liters per minute into the nebulizer container filled with the pentamidine isethionate solution and generates particles between 0.5 to 5 microns in conduit of aerosolized pentamidine; and
wherein the patients being treated draws on the mouthpiece drawing the air through the one-way valve, and the airstream entrains the pentamidine particles in the conduit;
wherein the airstream containing the pentamidine isethionate aerosol passes around the baffle of the one-way valve which baffle reduces the particles having a mean particle size larger than about 2 μm to the particles having a mean diameter in the range from about 1 to about 2 μm; and
wherein the patient draws the nebulized particles through the mouthpiece into the lungs.

* * * * *